(12) United States Patent
Denchokpraguy et al.

(10) Patent No.: US 10,689,806 B2
(45) Date of Patent: Jun. 23, 2020

(54) PRETREATMENT PROCESS OF LIGNOCELLULOSIC BIOMASS

(71) Applicant: PTT GLOBAL CHEMICAL PUBLIC COMPANY LIMITED, Chatuchak, Bangkok (TH)

(72) Inventors: Naphatsaya Denchokpraguy, Chatuchak (TH); Verawat Champreda, Chatuchak (TH); Navadol Laosiripojana, Chatuchak (TH)

(73) Assignee: PTT GLOBAL CHEMICAL PUBLIC COMPANY LIMITED, Chatuchak, Bangkok (TH)

( * ) Notice: Subject to any disclaimer, the term of this patent is extended or adjusted under 35 U.S.C. 154(b) by 399 days.

(21) Appl. No.: 15/516,251

(22) PCT Filed: Oct. 1, 2015

(86) PCT No.: PCT/TH2015/000063
§ 371 (c)(1),
(2) Date: Mar. 31, 2017

(87) PCT Pub. No.: WO2016/053209
PCT Pub. Date: Apr. 7, 2016

(65) Prior Publication Data
US 2017/0241076 A1    Aug. 24, 2017

(30) Foreign Application Priority Data
Oct. 1, 2014   (TH) ................................ 1401005962

(51) Int. Cl.
*C12P 19/02*    (2006.01)
*D21C 3/02*    (2006.01)
(Continued)

(52) U.S. Cl.
CPC ................ *D21C 3/02* (2013.01); *C12P 7/649* (2013.01); *C12P 19/02* (2013.01); *C13K 1/02* (2013.01);
(Continued)

(58) Field of Classification Search
USPC .......................................................... 162/72
See application file for complete search history.

(56) References Cited

U.S. PATENT DOCUMENTS

| | | | |
|---|---|---|---|
| 2010/0159520 A1* | 6/2010 | Diner | C08H 8/00 435/72 |
| 2013/0217868 A1 | 8/2013 | Fackler et al. | |
| 2013/0236933 A1 | 9/2013 | Huang et al. | |

FOREIGN PATENT DOCUMENTS

WO    2013/166469 A2    11/2013

OTHER PUBLICATIONS

International Search Report dated Oct. 1, 2014, issued in counterpart International Application No. PCT/TH2015/000063 (3 pages).

\* cited by examiner

*Primary Examiner* — Jacob T Minskey
(74) *Attorney, Agent, or Firm* — Westerman, Hattori, Daniels & Adrian, LLP (57) ABSTRACT

The present invention relates to a pretreatment process of lignocellulosic biomass, comprising contacting lignocellulosic biomass with pretreatment solution in a temperature ranging from an ambient temperature to 100° C. and a pressure of at least 20 bars, wherein the pretreatment solution comprising water, water-miscible organic solvent and alkali having a concentration of 5 to 15% w/v if the alkali is solid or 5 to 15% v/v if the alkali is liquid. Said pretreatment process operates in mild condition or at low temperature to (Continued)

be specified with the removing of lignin but not destroying cellulose and increasing desired sugar yield.

13 Claims, 9 Drawing Sheets

(51) Int. Cl.
*D21C 3/20* (2006.01)
*C13K 1/02* (2006.01)
*C12P 7/64* (2006.01)
*D21C 11/00* (2006.01)

(52) U.S. Cl.
CPC ............ *D21C 3/20* (2013.01); *D21C 11/0007* (2013.01); *C12P 2201/00* (2013.01); *Y02E 50/13* (2013.01); *Y02E 50/16* (2013.01)

PRETREATMENT PROCESS OF LIGNOCELLULOSIC BIOMASS

FIELD OF THE INVENTION

The present invention relates to a chemical field of lignocellulosic biomass technology.

BACKGROUND OF THE INVENTION

At present, biofuel production including industrial chemicals from agricultural lignocellulosic biomass has come to attentions because it's possibility in both technical and economic aspects. Basically, all agricultural lignocellulosic biomass including hardwood, softwood, and agricultural waste have lignocellulosic chemical structure which contains three main components which are: (1) cellulose which is linear polymer of glucose sugar connected to each other by 1,4-β-glycosidic bond and arranging in orderly fiber with high crystallization; (2) hemicellulose which is amorphous branched polymer composed mainly of pentose sugar such as xylose and arabinose and hexose sugar such as glucose, mannose, and galactose, including sugar derivatives, hemicellulose acting as a matrix in plant cell wall; and (3) lignin which is polymer of phenolic compounds arranging in three dimensional structure to provide strength to plant cell wall, including other minor components such as proteins, lipids, and minerals. Lignocellulosic structure is strong and durable to the physical, chemical, and biological degradations.

A sugar platform bio refinery process is a fuel and chemical production process with a high economic potential and environmental friendly. In this process, lignocellulosic biomass is digested into sugars with acids or enzymes. Obtained sugar is transformed into biofuel and other chemical products via fermentation or chemical catalytic processes. A pretreatment of agricultural lignocellulosic biomass is an important step for enhancing enzymatic digestibility of lignocellulosic biomass. Said pretreatment has direct effect on structure and chemical composition of lignocellulosic biomass which includes removing of hemicellulose, dissolving and extracting lignin, reducing polymer size of carbohydrate, and reducing crystallization of cellulose. These can result in accessibility of enzymes to cellulosic fiber, then yielding more sugar from enzymatic digestion. The pretreatment of lignocellulosic biomass can be done by chemical, thermal, and biological methods, each one has its technical and economic advantage and disadvantage and suitable for different physical structure and chemical basic character of lignocellulosic biomass.

The pretreatment of lignocellulosic biomass with organic solvent (Organosolv) is the effective process and can be applied to variety of lignocellulosic biomass in hardwood, softwood, and agricultural waste. Organic solvent can be selected from physical and chemical properties such as boiling point, polarity, including extraction specificity to lignin and hemicellulose. Ethanol and methanol are basic organic solvents in the pretreatment process of lignocellulosic biomass, whereas there have been studies on other organic solvents such as organic alkali, ketone, ester, 1,4-butanediol, butanol, and ethanolamine, including high boiling point organic solvent such as glycerol, ethylene, propylene glycol. Moreover, organic acids have been used such as formic acid, acetic acid, and peroxyformic acid. Most of the pretreatment processes using organic solvents have high selectivity which would not destroy cellulose and provide high quality and purity lignin which can be value added. Moreover, use of organic solvent reduces viscosity in the system and reduces re-precipitation of lignin on the surface of lignocellulosic biomass which is the current limitation of other pretreatment processes for lignocellulosic biomass.

The adding of catalyst is another study to increase effectiveness in pretreatment of lignocellulosic biomass using several thermochemical techniques such as high pressure steam, steam explosion, and high pressure hot water with several acids such as sulfuric acid, hydrochloric acid, and phosphoric acid, including organic acid such as oxalic acid for the increasing of efficiency and selectivity which lead to the reduction of temperature and energy consume in the pretreatment process. While the use of alkali such as sodium hydroxide, ammonia, and limestone provides high effectiveness for increasing of sugar yield from digestion of lignocellulosic biomass. The use of alkali as a catalyst results in lignin extraction including partial digestion of hemicellulose and gives expansion to cellulose.

The pretreatment process of lignocellulosic biomass using organic solvent under alkaline condition was disclosed in U.S. Pat. No. 8,460,898B2, which included the further adding of ammonia and pretreating at a temperature ranging of 100 to 220° C. to solubilize lignin in suspension then separating desired polysaccharide. Moreover, U.S. Pat. No. 8,278,070B2 disclosed the adding of organo-mercaptan in organic solvent under alkaline condition for the increasing the effectiveness of lignin extraction.

Patent publication no. WO 2013/151927 disclosed the pretreatment process of lignocellulosic biomass using a mixture of organic solvent, alkali, and oxidizing agent. This process increased effectiveness in the separation of polysaccharide from lignocellulosic biomass. However, the pretreatment process of lignocellulosic biomass using oxidizing agent gave unwanted by-product and effected to following steps of fermentation and sugar separation.

Therefore, the pretreatment process of lignocellulosic biomass has been further developed under low temperature condition or mild condition for the specificity of removing of lignin but not destroying cellulose, including the reduction of by-product which effects the further steps in sugar production.

SUMMARY OF THE INVENTION

This invention aims to develop a pretreatment process of lignocellulosic biomass under mild condition or at low temperature to be specified with the removing of lignin but not destroying cellulose and increasing desired sugar yield. Said process comprises contacting lignocellulosic biomass with pretreatment solution in a temperature ranging from an ambient temperature to 100° C. and a pressure of at least 20 bars, wherein the pretreatment solution comprising water, water-miscible organic solvent and alkali having a concentration of 5 to 15% w/v if the alkali is solid, or 5 to 15% v/v if the alkali is liquid.

DETAILED DESCRIPTION OF THE INVENTION

Definition

Technical terms or scientific terms used herein, unless stated otherwise, have their definitions as known in persons skilled in the art.

Any tool, equipment, method, or chemical mentioned herein shall mean tool, equipment, method, or chemical being used or practiced generally by a person skilled in the art of this field unless stated otherwise that they are tools, equipment, methods, or chemicals specific only in this invention.

Use of singular nouns or pronouns when used with "comprising" in claims and/or specification means "one" and will also include "one or more", "at least one", and "one or more than one".

Throughout this application, the term "about" used to indicate any value that is appeared or expressed herein may be varied or deviated, which the variation or deviation may occur from the error of instruments and methods used to determine various values.

An objective of this invention is to develop a pretreatment process of lignocellulosic biomass with pretreatment solution comprising water, water-miscible organic solvent and alkali having a concentration of 5 to 15% w/v if the alkali is solid, or 5 to 15% v/v if the alkali is liquid. The pretreatment process operates in mild condition or at low temperature.

Hereafter, invention embodiments are shown without any purpose to limit any scope of the invention.

This invention relates to the pretreatment process of lignocellulosic biomass comprising contacting lignocellulosic biomass with pretreatment solution in a temperature ranging from an ambient temperature to 100° C. and a pressure of at least 20 bars, wherein the pretreatment solution comprising water, water-miscible organic solvent and alkali having a concentration of 5 to 15% w/v if the alkali is solid, or 5 to 15% v/v if the alkali is liquid. Preferable, the alkali has a concentration of 5 to 12% w/v if the alkali is solid or 5 to 12% v/v if the alkali is liquid.

In one aspect, the water-miscible organic solvent is selected from acetone, ethanol, ethyl acetate, or a mixture thereof. Most preferable, said organic solvent is acetone.

Preferably, a concentration of the water-miscible organic solvent is in a range of 70 to 95% v/v. More preferable is in a range of 80 to 90% v/v.

Preferred alkali is selected from sodium hydroxide, ammonium hydroxide, triethylamine, or a mixture thereof. Most preferable, said alkali is sodium hydroxide.

In another aspect of the invention, a temperature of the pretreatment process of lignocellulosic biomass is ranging from an ambient temperature to 100° C. Preferable the temperature is in the range of 50 to 80° C.

In another aspect of the invention, a pretreatment time of lignocellulosic biomass is not more than 60 minutes. Preferable it is 5 to 30 minutes starting after system reaches targeted temperature.

The pretreatment process of lignocellulosic biomass may further comprise stirring at a speed rate ranging from 250 to 300 rpm.

The lignocellulosic biomass in dry form is in a range of 2 to 9% w/v of the pretreatment solution. The lignocellulosic biomass may be selected from rice straw, bagasse, corncob, corn fiber, pineapple husk, or bamboo.

The followings are examples of a preparation of lignocellulosic biomass before pretreatment process, a pretreatment process according to the invention, and an analysis of sugar yielded from pretreatment.

The preparation step of biomass could be done by the reduction of rice straw size using cutting machine and sizing using 2 mm mesh.

The pretreatment of lignocellulosic biomass obtained from biomass preparation step was performed in 600 mL, high pressure stainless steel reactor (Parr reactor 4848, Parr instrument, USA) equipped with thermometer inside. The pretreatment process comprises of feeding of lignocellulosic biomass which was 4 grams of rice straw, 160 mL acetone, and 200 mL of 5% w/v of sodium hydroxide solution. Then, nitrogen gas was purged into the system to have initial pressure of 20 bars. Then, the system was heated at about 80° C. for 30 minutes starting after the system had reached targeted temperature. After that, the pretreatment process was stopped by reducing temperature such as submerging reactor into water or any other coolants. Then, filtration had been performed to separate solid and liquid parts. The solid part was put into the oven at 60° C.

The analysis of sugar content yielded from the pretreatment process was done. The above obtained solid part was digested by adding 20 FPU/g of cellulose enzyme (Accellerase 1500, Genecor, USA) in 50 mmol sodium acetate buffer with pH of 4.8. The said solid part was then incubated at a temperature of 50° C. for 72 hours with tube shaking at a speed rate of about 30 rpm. The liquid part was collected as sample for quantitative of reducing sugar using dinitrosalicylic acid method (Miller 1959).

Note: FPU of cellulase enzymes was obtained from the digestion of filter paper obtained from the analysis according to standard method (Adney and Baker 1996).

The quantitative of reducing sugar after enzymatic digesting could be determined using high performance liquid chromatography (HPLC) method (Water e2695, Water, USA), equipped with differential refractometer, and Aminex HPX-87H column (Bio-Rad, USA). The compositions in liquid part were treated with acid and digested by a method according to NREL standard. Glucose yield was calculated into theoretical percentage comparing to cellulose content in starting biomass in dry form, which was 358 mg/g (×1.11).

Effect of the Pretreatment Using Pretreatment Solutions Having Different Alkali 4 grams of rice straw, equally to 2% w/v was exposed to a pretreatment solution comprising 160 mL acetone and sodium hydroxide, ammonium hydroxide, and triethylamine wherein the concentration of the alkali was 5% w/v (for sodium hydroxide), or 5% v/v (for ammonium hydroxide and triethylamine). The pretreatment process was performed at a temperature around 80° C. for about 30 minutes at initial pressure around 20 bars with a speed rate of stirring at 250 rpm.

Figure 1:
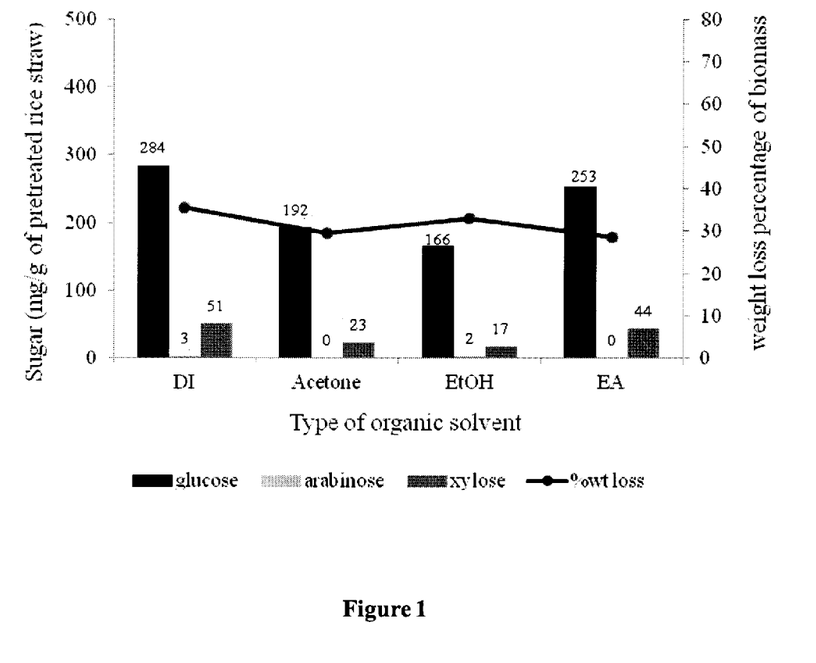
FIG. 1 shows an effect of ammonium hydroxide in various solvents (distilled water (DI); acetone; ethanol (EtOH); and ethyl acetate (EA): to sugar yield from digestion of enzymatic pretreatment solid.
Figure 2:
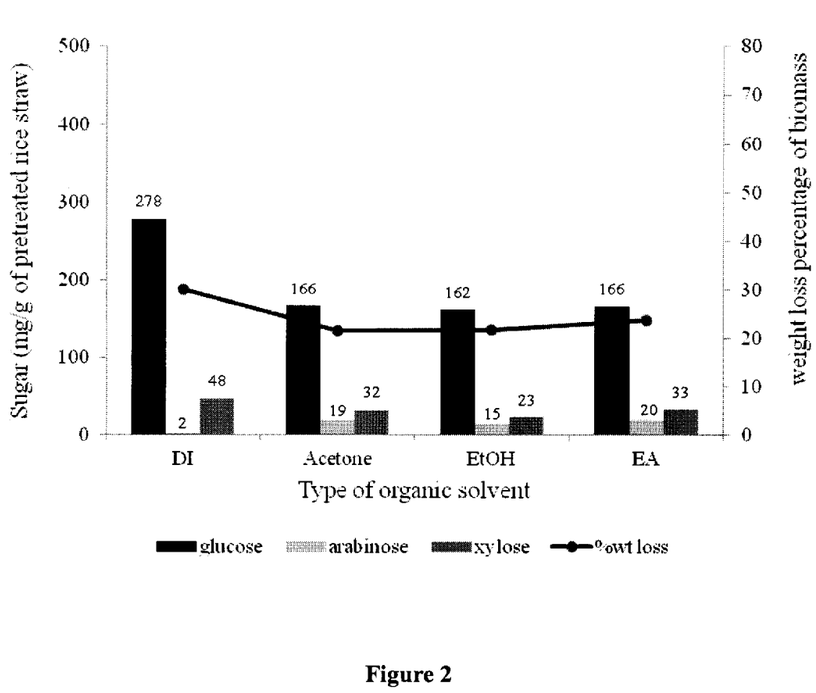
FIG. 2 shows an effect of triethylamine in various solvents (DI; acetone; EtOH; and EA) to sugar yield from digestion of enzymatic pretreatment solid.
Figure 3:
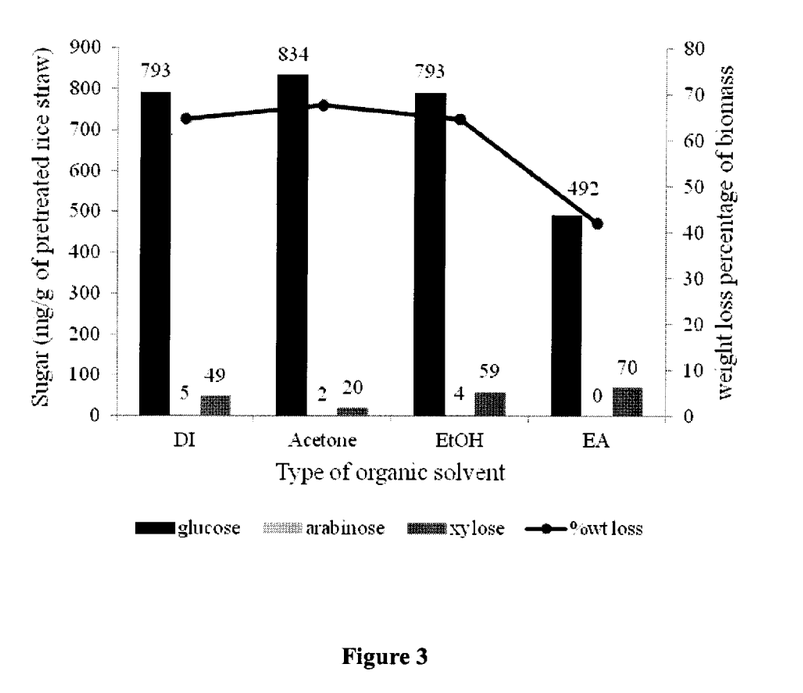
FIG. 3 shows an effect of sodium hydroxide in various solvents (DI; acetone; EtOH; and EA) to sugar content from digestion of enzymatic pretreatment solid.

From table 1 and FIGS. 1, 2, and 3, it was found that the use of different alkali catalysts increases solid digestibility of pretreatment process comparing to without alkali catalyst. The process without catalyst provided maximum reducing sugar from enzymatic digestion of 146 mg/g comprising 131 mg of glucose per gram of pretreated dry biomass which is equal to 26.7% of glucose theoretical yield. The use of sodium hydroxide provided the best pretreatment effect, giving 75.6% of glucose theoretical yield, provided maximum reducing sugar from enzymatic digestion of 865 mg/g comprising 834 mg of glucose per gram of pretreated dry biomass, whereas the use of ammonium hydroxide and triethylamine provided 34.3% and 33.0% of glucose theoretical yields respectively. This test showed the effect of alkali catalysts in the pretreatment process of lignocellulosic biomass using a mixture of organic solvent. These results were compared to the use of hydrogen peroxide as an oxidizing agent in the pretreatment. Results showed that hydrogen peroxide could react with acetone to become acetone peroxide which was very reactive and could lead to explosion which was not suitable to be used with acetone.

TABLE 1

Effect of pretreatment solutions, pretreatment of lignocellulosic biomass and different alkali catalysts in acetone to sugar content from enzymatic digestion

| Type of alkali in pretreatment solution | Reducing sugar (mg/g pretreated biomass) | Glucose (mg/g pretreated biomass) | % weight loss of biomass | Theoretical percentage of glucose |
|---|---|---|---|---|
| — | 146 | 131 | 19 | 26.7 |
| Sodium hydroxide | 856 | 834 | 64 | 75.6 |
| Ammonium hydroxide | 215 | 192 | 29 | 34.3 |
| Triethylamine | 217 | 166 | 21 | 33.0 |

Effect of Temperature to the Pretreatment Process of Lignocellulosic Biomass

This experiment studied the effect of sodium hydroxide in the pretreatment process of lignocellulosic biomass using acetone in various target temperatures ranging from about 50 to 100° C. 2% w/v of rice straw in dry form of 2% w/v was expose to pretreatment solution comprising 160 mL acetone and 5% weight by final volume of sodium hydroxide, pretreatment process was performed for 30 minutes at initial pressure of 20 bars, with stirring speed at 250 rpm.

Figure 4:
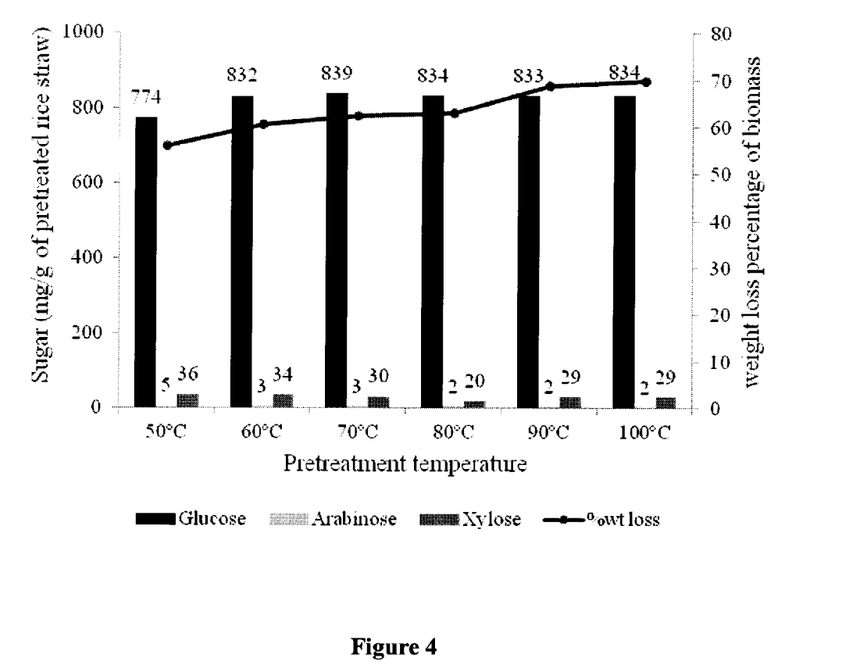
FIG. 4 shows an effect of pretreatment process temperature to sugar yield from digestion of enzymatic pretreatment solid.

From table 2 and FIG. 4, it was found that pretreatment at about 50° C. gave highest glucose of 85.7% theoretically yield comparing to cellulose in native biomass. Reducing sugar obtained from enzymatic digestion was 815 mg, containing 774 mg of glucose per g of pretreated dry biomass. Sugar content in the term of glucose theoretically yield percentage obtained from the use of sodium hydroxide as catalyst was higher than without catalyst and the use of ammonium hydroxide and triethylamine under same conditions at 80 to 100° C.

TABLE 2

Effect of temperature to sugar content obtained from solid enzymatic digestion after pretreatment

| Temperature (° C.) | Reducing sugar (mg/g pretreated) | Glucose (mg/g pretreated) | Weight loss percentage of biomass | Theoretical percentage of glucose yield |
|---|---|---|---|---|
| 50 | 815 | 774 | 56 | 85.7 |
| 60 | 870 | 832 | 61 | 81.6 |
| 70 | 872 | 839 | 62 | 80.2 |
| 80 | 856 | 834 | 64 | 75.6 |
| 90 | 864 | 833 | 69 | 64.9 |
| 100 | 865 | 834 | 70 | 63.0 |

Effect of the Content of Water-Miscible Organic Solvent

The effect of the amount of water-miscible organic solvent in pretreatment process using sodium hydroxide as a catalyst was studies. 2% w/v of rice straw in dry form was exposed to pretreatment solution comprising acetone from 160 to 180 mL and sodium hydroxide. Then water was added until the volume of the solution is 200 mL, so that acetone concentration was 80 to 90% v/v. The concentration of alkali was 5% w/v. The pretreatment process was performed at temperature around 80° C. for about 30 minutes at initial pressure of 20 bars with stirring speed at about 250 rpm.

Figure 5:
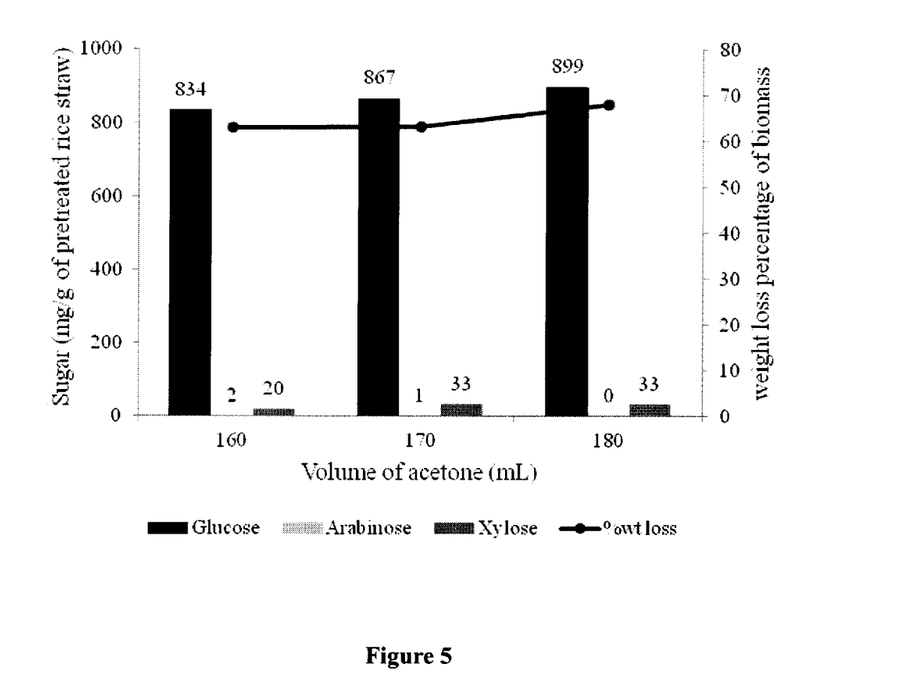
FIG. 5 shows an effect of organic solvent content in pretreatment process to sugar yield from digestion of enzymatic pretreatment solid.

From table 3 and FIG. 5, it was found that the concentration of acetone effected sugar yield from enzymatic digestion step. Acetone having a concentration of 85% v/v gave highest glucose theoretically yield of 80.7% comparing to cellulose content in native biomass. Reducing sugar from enzymatic digestion step was 902 mg with 867 mg of glucose per g of pretreated dry biomass.

TABLE 3

Effect of acetone ratio to sugar content obtained from enzymatic digestion

| Acetone concentration percentage | Reducing sugar (mg/g pretreated biomass) | Glucose (mg/g pretreated biomass) | Weight loss percentage of biomass | Theoretical yield percentage of glucose |
|---|---|---|---|---|
| 80 | 856 | 834 | 64 | 75.6 |
| 85 | 902 | 867 | 63 | 80.7 |
| 90 | 933 | 899 | 68 | 72.4 |

Effect of Alkali Concentration

Effect of concentration of sodium hydroxide in the pretreatment process of rice straw using acetone was studied in this experiment. 2% w/v of dry rice straw was exposed to the pretreatment solution comprising 160 mL acetone and sodium hydroxide at various concentrations ranging from 5 to 10% w/v. The pretreatment process was performed at temperature around 80° C. for about 30 minutes at initial pressure of 20 bars with stirring speed at about 250 rpm.

Figure 6:
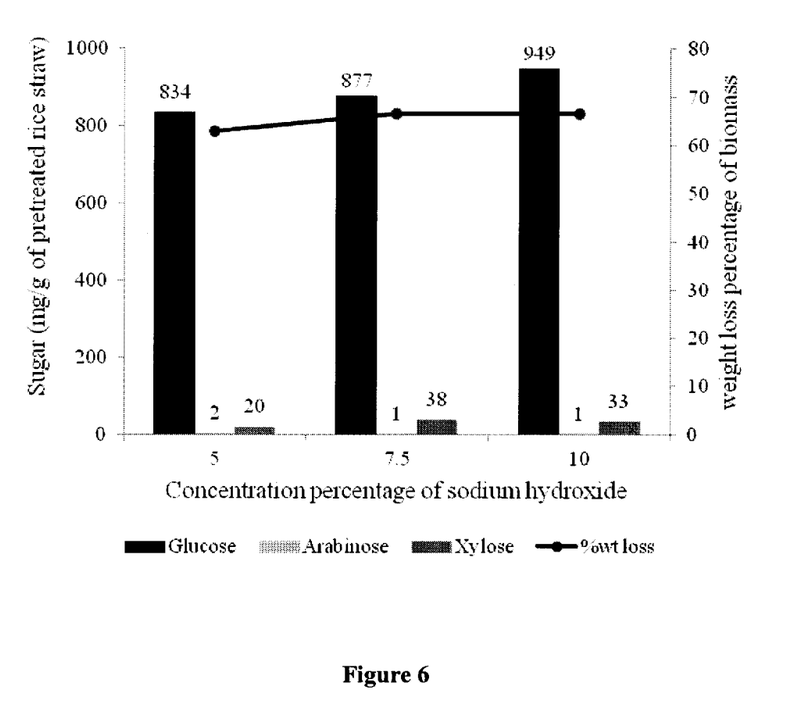
FIG. 6 shows an effect of sodium hydroxide in pretreatment process to sugar yield from digestion of enzymatic pretreatment solid.

From table 4 and FIG. 6, it was found that increasing of sodium hydroxide concentration gave higher sugar yield from enzymatic digestion step. Sodium hydroxide at concentration of 10% w/v gave highest glucose at 83.6% theoretically yield comparing to cellulose content in native biomass. Reducing sugar from enzymatic digestion step was 982 mg with 949 mg of glucose per g of pretreated dry biomass.

TABLE 4

Effect of sodium hydroxide concentration to sugar obtained from enzymatic digestion

| Sodium hydroxide concentration (%) | Reducing sugar (mg/g pretreated biomass) | Glucose (mg/g pretreated biomass) | Weight loss percentage of biomass | Theoretical yield percentage of glucose |
|---|---|---|---|---|
| 5 | 856 | 834 | 64 | 75.6 |
| 7.5 | 916 | 877 | 66 | 75.0 |
| 10 | 982 | 949 | 65 | 83.6 |

Effect of Time to the Pretreatment Process of Lignocellulosic Biomass

This experiment studied the effect of sodium hydroxide in pretreatment process of lignocellulosic biomass using acetone at pretreatment of 0 to 60 minutes. 2% w/v of dry rice straw was exposed to the pretreatment solution comprising 180 mL acetone and sodium hydroxide at concentration from 5 to 7% w/v. The pretreatment process was performed at temperature around 80° C. at initial pressure of 20 bars with stirring speed at about 250 rpm. Time was counting after the system reached its targeted temperature.

Figure 7:
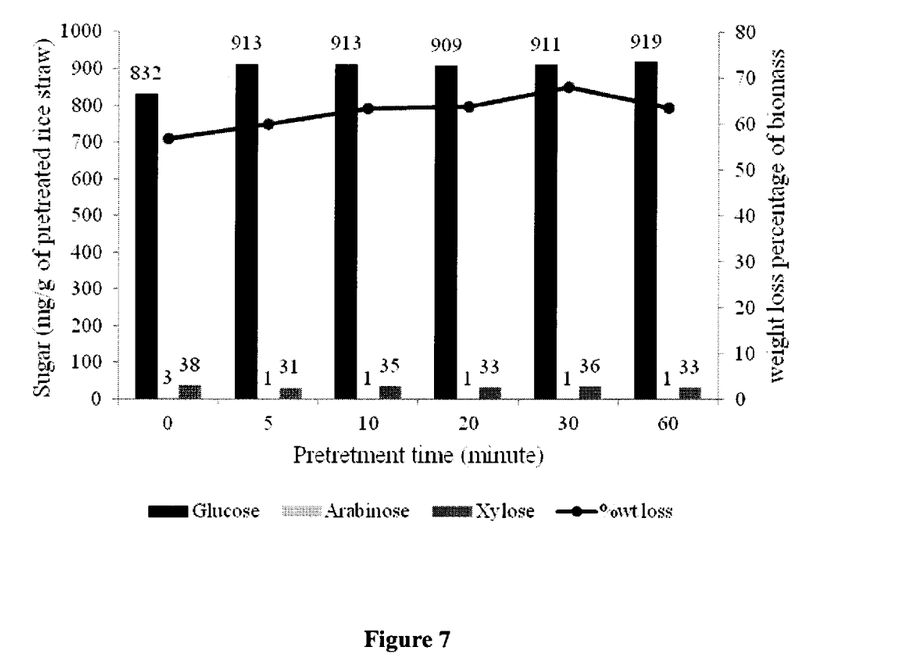
FIG. 7 shows an effect of pretreatment process time to sugar yield from digestion of enzymatic pretreatment solid, wherein alkali with a concentration of 5% w/v was used in pretreatment process.
Figure 8:
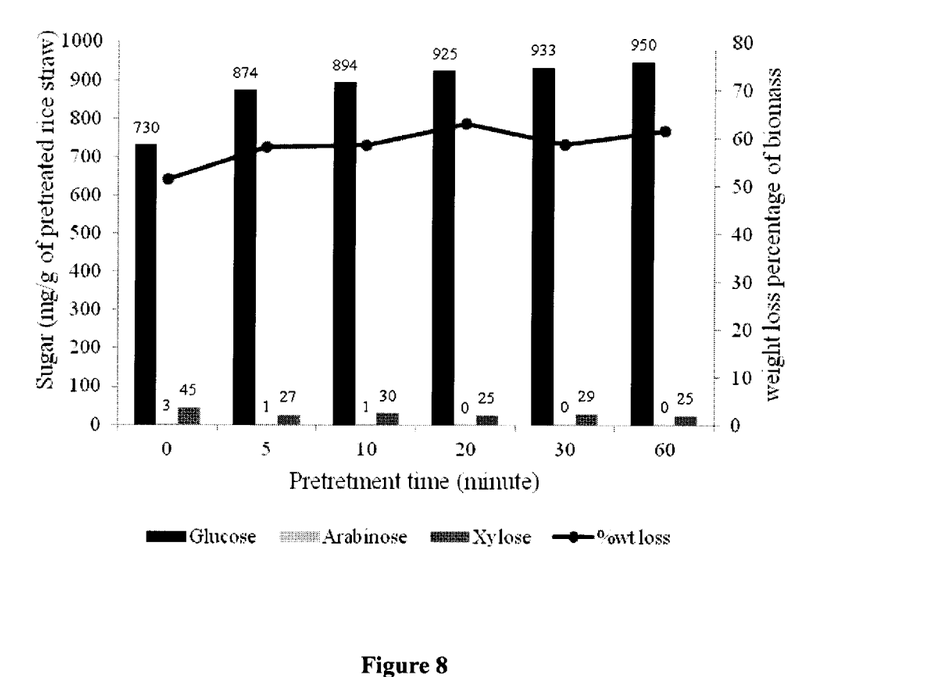
FIG. 8 shows an effect of pretreatment process time to sugar yield from digestion of enzymatic pretreatment solid, wherein alkali with a concentration of 7% w/v was used in pretreatment process.

From table 5 and 6 and FIGS. 7 and 8, it was found that increasing of time gave higher sugar yield from enzymatic digestion step. However, when comparing with cellulose content in native biomass, it was found that at alkali concentration of 5%, pretreatment at 5 minutes gave highest glucose of 91.9% theoretically yield comparing to cellulose content in native biomass. Reducing sugar from enzymatic digestion step was 945 mg with 913 mg of glucose per g of pretreated dry biomass. Whereas when alkali concentration was 7%, pretreatment at 30 minutes gave highest glucose of 96.3% theoretically yield comparing to cellulose content in native biomass. Reducing sugar from enzymatic digestion step was 962 mg with 933 mg of glucose per g of pretreated dry biomass.

TABLE 5

Effect of time to sugar obtained from enzymatic digestion (at alkali concentration of 5% w/v)

| Time (minute) | Reducing sugar (mg/g pretreated biomass) | Glucose (mg/g pretreated biomass) | Weight loss percentage of biomass | Theoretical yield percentage of glucose |
|---|---|---|---|---|
| 0 | 873 | 832 | 57 | 90.0 |
| 5 | 945 | 913 | 60 | 91.9 |
| 10 | 949 | 913 | 63 | 85.0 |
| 20 | 943 | 909 | 64 | 82.3 |
| 30 | 948 | 911 | 67 | 75.7 |
| 60 | 953 | 919 | 64 | 83.3 |

TABLE 6

Effect of time to sugar obtained from enzymatic digestion (at alkali concentration of 7% w/v)

| Time (minute) | Reducing sugar (mg/g pretreated biomass) | Glucose (mg/g pretreated biomass) | Weight loss percentage of biomass | Theoretical yield percentage of glucose |
|---|---|---|---|---|
| 0 | 779 | 730 | 51 | 90.0 |
| 5 | 902 | 874 | 58 | 92.4 |
| 10 | 925 | 894 | 59 | 92.2 |
| 20 | 950 | 925 | 63 | 86.1 |
| 30 | 962 | 933 | 59 | 96.3 |
| 60 | 974 | 950 | 61 | 93.2 |

Effect of Biomass Content

In this experiment, effect of biomass content in starting solid matter in the pretreatment process using pretreatment solution comprising sodium hydroxide and acetone was studied. 2 to 9% w/v of dry rice straw was exposed to the pretreatment solution comprising 180 mL acetone and sodium hydroxide at concentration of 5% w/v. The pretreatment process was performed at temperature around 80° C. for about 30 minutes at initial pressure of 20 bars with stirring speed at about 250 rpm.

Figure 9:
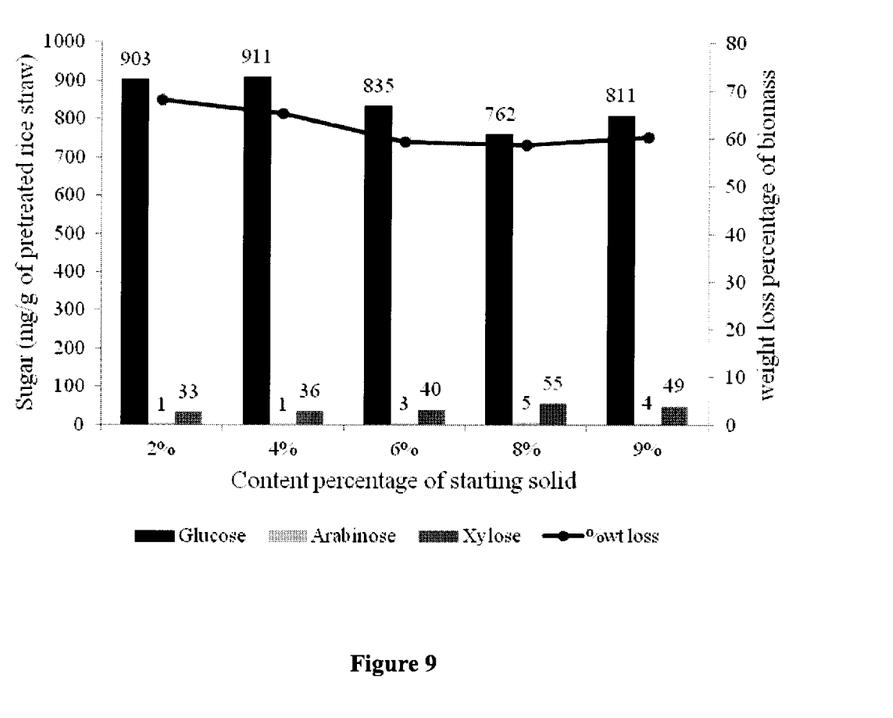
FIG. 9 shows an effect of starting solid content in system to sugar yield from digestion of enzymatic pretreatment solid.

From table 7 and FIG. 9, it was found that increasing of starting solid content affected the sugar yield from enzymatic digestion step. The use of 6% w/v of starting solid matter gave highest glucose of 86.2% theoretically yield comparing to cellulose content in native biomass. Reducing sugar from enzymatic digestion step was 878 mg with 835 mg of glucose per g of pretreated dry biomass.

TABLE 7

Effect of starting solid matter in the system to sugar yield obtained from enzymatic digestion

| Starting solid matter (%) | Reducing sugar (mg/g pretreated biomass) | Glucose (mg/g pretreated biomass) | Weight loss percentage of biomass | Theoretical yield percentage of glucose |
|---|---|---|---|---|
| 2 | 938 | 903 | 68 | 72.7 |
| 4 | 948 | 911 | 67 | 75.7 |
| 6 | 878 | 835 | 59 | 86.2 |
| 8 | 822 | 762 | 59 | 78.6 |
| 9 | 865 | 811 | 60 | 81.6 |

BEST MODE OF THE INVENTION

Best mode or preferred embodiment of the invention is as provided in the description of the invention.

The invention claimed is:

1. A pretreatment process of lignocellulosic biomass consisting essentially of contacting lignocellulosic biomass with pretreatment solution in a temperature ranging from an ambient temperature to 100° C. and a pressure of at least 20 bars, wherein the pretreatment solution
    consisting essentially of water, water-miscible organic solvent and alkali having a concentration of 5 to 15% w/v if the alkali is solid or 5 to 15% v/v if the alkali is liquid;
    wherein the water-miscible organic solvent consists essentially of at least one of the group consisting of acetone, ethanol, and ethyl acetate.

2. The process according to claim 1, wherein the alkali having a concentration of 5-12% w/v if the alkali is solid or 5-12% v/v if the alkali is liquid.

3. The process according to claim 1, wherein the temperature is in the range of 50 to 80° C.

4. The process according to claim 1, wherein the water-miscible organic solvent is acetone.

5. The process according to claim 1, wherein a concentration of the water-miscible organic solvent is in a range of 70 to 95% v/v.

6. The process according to claim 5, wherein the concentration of the water-miscible organic solvent is in the range of 80 to 90% v/v.

7. The process according to claim 1 or 2, wherein the alkali is selected from sodium hydroxide, ammonium hydroxide, triethylamine, or a mixture thereof.

8. The process according to claim 7, wherein the alkali is sodium hydroxide.

9. The process according to claim 1, wherein pretreatment time of lignocellulosic biomass is not more than 60 minutes.

10. The process according to claim 9, wherein the pretreatment time of lignocellulosic biomass is in range of 5 to 30 minutes.

11. The process according to claim 1, wherein said process further comprising stirring at a speed rate ranging from 250 to 300 rpm.

12. The process according to claim 1, wherein lignocellulosic biomass in dry form is in a range of 2 to 9% w/v of the pretreatment solution.

13. The process according to claim 1, wherein lignocellulosic biomass is selected from rice straw, bagasse, corncob, corn fiber, pineapple husk, or bamboo.

* * * * *